United States Patent [19]

Drake et al.

[11] Patent Number: 4,793,997
[45] Date of Patent: Dec. 27, 1988

[54] CONTROLLED DELIVERY DEVICE

[75] Inventors: Cyril F. Drake, Harlow; Alfred J. Arch, Ongar, both of England

[73] Assignee: Standard Telephone Cables Public Ltd. Co., London, England

[21] Appl. No.: 68,787

[22] Filed: Jun. 29, 1987

Related U.S. Application Data

[63] Continuation of Ser. No. 845,580, Mar. 28, 1986, abandoned.

[30] Foreign Application Priority Data

Mar. 28, 1985 [GB] United Kingdom ............... 8508173

[51] Int. Cl.$^4$ ................. A61K 9/00; A01N 11/04
[52] U.S. Cl. ....................... 424/426; 424/457;
514/770; 428/321.5; 428/34.4; 428/34.6
[58] Field of Search ............ 514/770, 962; 424/457,
424/9, 426; 501/45; 252/408.1; 428/321.5, 35,
36, 426

[56] References Cited

U.S. PATENT DOCUMENTS

| | | | |
|---|---|---|---|
| 4,218,255 | 8/1980 | Bajpai et al. | 501/134 |
| 4,283,227 | 8/1981 | Drake | 424/426 |
| 4,349,025 | 9/1982 | Drake | 424/426 |
| 4,350,675 | 9/1982 | Drake | 424/9 |
| 4,407,786 | 10/1983 | Drake et al. | 424/426 |
| 4,449,981 | 5/1984 | Drake et al. | 424/426 |
| 4,473,545 | 9/1984 | Drake et al. | 424/442 |
| 4,482,541 | 11/1984 | Telfer et al. | 424/128 |
| 4,517,006 | 5/1985 | Drake et al. | 424/426 |
| 4,519,866 | 5/1985 | Stol | 428/321.5 |
| 4,587,267 | 5/1986 | Drake et al. | 424/426 |
| 4,645,749 | 2/1987 | Drake | 501/45 |
| 4,662,879 | 5/1987 | Drake et al. | 424/438 |
| 4,678,659 | 7/1987 | Drake et al. | 424/451 |

Primary Examiner—Ellis P. Robinson
Assistant Examiner—P. J. Ryan
Attorney, Agent, or Firm—Kerkam, Stowell, Kondracki & Clarke

[57] ABSTRACT

A device for the controlled release of an active material into an aqueous medium, e.g. body fluids, comprises a water soluble glass container in which the active material is sealed. The container wall has a region of reduced thickness which region dissolves before the remainder of the container wall to release the active material.

7 Claims, 2 Drawing Sheets

CONTROLLED DELIVERY DEVICE

This is a continuation of application Ser. No. 845,580, filed Mar. 28, 1986 now abandoned.

This invention relates to devices for the controlled release of an active material into an aqueous medium.

Active materials can be released, after a predetermined delay, into an aqueous medium by sealing the material in a tube of a water soluble glass. On exposure to the aqueous medium the glass dissolves at a predetermined rate and releases its contents when dissolution of the tube wall has taken place. Such a technique is described for example in our published specification No. 2,079,152 B.

A disadvantage of this technique is the difficulty of accurate prediction of the period before release is effected. This period is of course proportioned to the tube wall thickness but is affected by a variety of factors. The most important of these are non-concentricity of the tube and the extreme fragility of the tube shortly before complete dissolution, i.e. the tube may collapse to release its contents before dissolution is complete. Both these factors reduce the expected delay period by an unpredictable amount.

The object of the present invention is to minimise or to overcome this disadvantage.

According to one aspect of the invention there is provided a device for the release of an active material into an aqueous medium, the device including a sealed container of a water soluble glass in which the active material is encapsulated, said container being so constructed that, on exposure to water, a portion only of the container is selectively breached by dissolution to release the container contents after a predetermined period.

According to the invention there is further provided a device for the release of an active material into an aqueous medium, the device including a sealed container of a water soluble glass in which the active material is encapsulated, wherein said container has a region of reduced resistance to solution attack whereby, in use, the release time of the active material is determined.

By providing the capsule with a weak point, dissolution of a portion of the wall to release the contents is effected whilst the remainder of the wall remains self supporting. This ensures that the release time can be accurately predetermined.

Embodiments of the invention will now be described with reference to the accompanying drawings, in which.

Figure 1A:
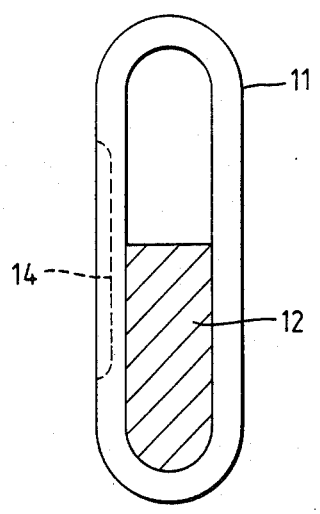
FIGS. 1a and 1b are respectively cross-sectional and longitudinal sectional views of a capsule for release of an active material.
Figure 1B:
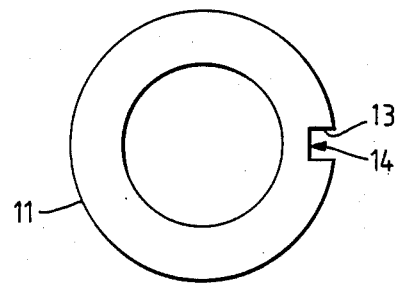
Figure 7:
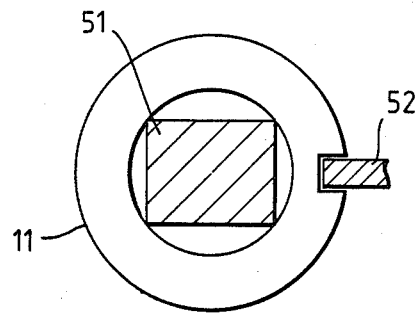

and FIG. 7 illustrates a method of making the capsule of FIGS. 1a and 1b.

Referring to FIGS. 1a and 1b, the controlled release device comprises a tubular capsule 11 formed from a water soluble glass composition and containing a quantity of an active material 12. The wall of the capsule is provided e.g. with a longitudinal groove 13 whereby a region 14 of reduced wall thickness, i.e. of reduced resistance to solution attack, is provided. The dissolution time of the capsule wall is determined both by the thickness of the region 14 and the dissolution rate of the glass from which the capsule is made. When the capsule is exposed to an aqueous medium the whole capsule wall is dissolved at a constant rate. After a predetermined period the region 14 is completely dissolved thus releasing the capsule contents. As only this small portion of the capsule wall is dissolved away the remainder of the capsule remains self supporting.

Figure 2:
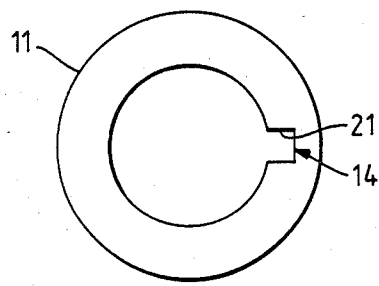
FIGS. 2, 3, 4, 5 and 6 are sectional views of alternative capsules.
Figure 3:
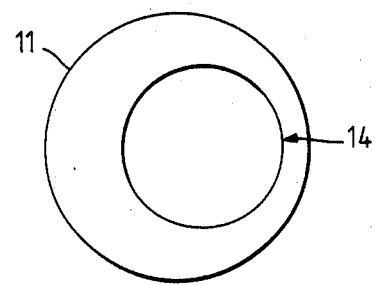
Figure 4:
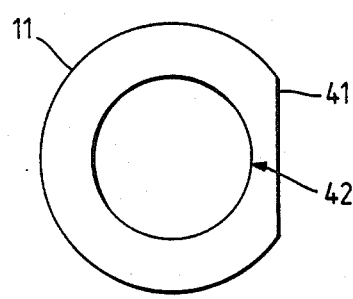

An alternative device construction is shown in FIG. 2. In this arrangement a groove 21 is provided on the internal wall of the capsule. A further technique is shown in FIG. 3, wherein a considerable degree of non-concentricity between the internal and external surfaces of the tube bore is provided. This determines a region of minimum wall thickness which in turn determines the dissolution time of the device. Another construction is shown in FIG. 4. The wall 11 of the capsule is cut away to form a flat portion 41 defining a reduced thickness region 42 whose thickness determines the dissolution time.

Figure 5:
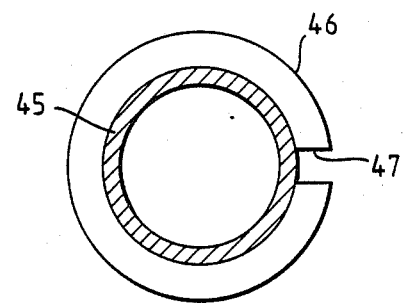

In a further application (FIG. 5) the capsule wall may comprise an inner layer 45 of a glass of relatively high dissolution rate and an outer layer 46 of a glass of relatively low dissolution rate. A region of reduced wall thickness, e.g. a groove or depression 47, extends substantially or completely through the outer layer 46 so that dissolution through the inner layer 45 can take place whilst the outer layer remains self supporting.

Figure 6:
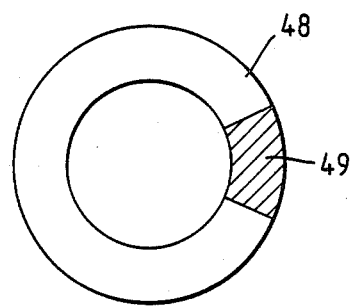

A further embodiment is shown in FIG. 6. In this device the wall of the capsule comprises a first glass 48 of relatively low dissolution rate and a second glass 49, forming a sector of the wall, of a relatively high dissolution rate. When the device is exposed to an aqueous medium the sector comprising the high solubility glass 49 dissolves preferentially to release the capsule contents.

A technique for forming the groove of the device of FIG. 1 is shown in FIG. 6. The tube 11, prior to filling and sealing, is mounted on a square section mandrel 41 on which the tube is a sliding fit. The tube 11 is held by the mandrel 51 against a cutting wheel 52 whereby the groove is formed. The depth of the groove is determined by the distance between the mould 51 and the wheel 52 thus providing a high degree of accuracy.

In an alternative fabrication process the tubes of FIGS. 1 to 6 may be formed by drawing from a cast or moulded preform, the cross-section of the tube corresponding to the preform cross-section. Such techniques are well known to those skilled in the glass processing art.

A wide variety of water soluble glass compositions may be used. However, for medical or veterinary applications we prefer to employ phosphorus pentoxide/alkali metal glasses modified by the addition of calcium oxide, magnesium oxide, zinc oxide or mixtures thereof. The glass may also contain trace quantities of therapeutic elements in oxide form.

The active material typically comprise a drug or medicament for release into the body fluids of the host into which it is implanted or ingested.

The following example illustrates the invention:

A water soluble glass was prepared by fusion of a mixture of sodium oxide, magnesium oxide, calcium oxide and phosphorus pentoxide to form a homogeneous material. Analysis of the glass showed its composition to be

| | |
|---|---|
| $Na_2O$ | 40.3 mole percent |
| $MgO$ | 8.8 mole percent |

| | |
|---|---|
| CaO | 7.8 mole percent |
| P$_2$O$_5$ | 43.0 mole percent |

The glass was cast into eccentric bore cylindrical tube stock having an outside diameter of 27 mm, an inner diameter of 15.5 mm. The bore was offset to provide a thinnest wall thickness of 2.6 mm. Portions of this stock were drawn down the tubing having an outer diameter of 2 mm and a wall thickness of 0.2 mm at its thinnest point.

The drawn tube was cut into 10 mm sections, each of which was filled with methylene blue powder and sealed at both ends. The sealed tubes were immersed in distilled water of pH 6.5 at 38° C. and the time taken ($T_d$) for dissolution of the thin portion of the wall to release the dye was measured.

From a sample of 20 tubes the average dissolution time $T_d$ was found to be 49.4 h with a standard deviation of 1.1 h or 2.2%. This demonstrates the close accuracy with which the dissolution time may be predetermined.

We claim:

1. A device for the timed release of an active material into an aqueous medium, the device comprising a sealed container having a wall consisting of a water soluble glass and in which container the active material is encapsulated, wherein a minor proportion of container wall consists of a region of reduced resistance to solution attack whereby, when the device is contacted by the aqueous medium, that region is dissolved over a predetermined time period to provide an opening in the container wall so as to release the active material whilst the remainder of the glass container wall is only partially dissolved so as to prevent collapse of the container.

2. A device as claimed in claim 1, wherein the reduced resistance region comprises a region of reduced wall thickness.

3. A device as claimed in claim 2, wherein said reduced thickness region comprises a groove provided in the device wall.

4. A device as claimed in claim 1, wherein the glass is a phosphorus pentoxide glass.

5. A device as claimed in claim 1, wherein the glass is a phosphorus pentoxide glass.

6. A device as claimed in claim 4, wherein said glass includes a modifying oxide selected from the group comprising calcium oxide, zinc oxide and mixtures thereof.

7. A device for the timed release of an active material into an aqueous medium, the device comprising a sealed tubular container having a wall consisting of a water soluble glass and in which container the active material is encapsulated, wherein the container wall has cylindrical inner and outer major surfaces, the two cylindrical surfaces being non co-axial so as to provide a region of reduced thickness in the container wall whereby, when the device is contacted by the aqueous medium, the region of reduced wall thickness is dissolved to provide an opening in the container wall so as to release the active material whilst the remainder of the container wall is only partially dissolved so as to prevent collapse of the container.

* * * * *